(12) United States Patent
Lai et al.

(10) Patent No.: US 7,284,862 B1
(45) Date of Patent: Oct. 23, 2007

(54) OPHTHALMIC ADAPTIVE-OPTICS DEVICE WITH A FAST EYE TRACKER AND A SLOW DEFORMABLE MIRROR

(75) Inventors: Ming Lai, Webster, NY (US); Mei Juan Yuan, Webster, NY (US)

(73) Assignee: MD Lasers & Instruments, Inc., Pleasanton, CA (US)

( * ) Notice: Subject to any disclaimer, the term of this patent is extended or adjusted under 35 U.S.C. 154(b) by 414 days.

(21) Appl. No.: 10/988,064

(22) Filed: Nov. 13, 2004

Related U.S. Application Data

(60) Provisional application No. 60/520,374, filed on Nov. 13, 2003.

(51) Int. Cl.
*A61B 3/14* (2006.01)
*A61B 3/10* (2006.01)

(52) U.S. Cl. ..................... 351/209; 351/211

(58) Field of Classification Search ............ 351/209, 351/210
See application file for complete search history.

(56) References Cited

U.S. PATENT DOCUMENTS

| | | | |
|---|---|---|---|
| 5,632,742 A | 5/1997 | Frey et al. | |
| 5,645,550 A | 7/1997 | Hohla | |
| 5,777,719 A | 7/1998 | Williams et al. | |
| 5,782,822 A | 7/1998 | Telfair et al. | |
| 5,949,521 A | 9/1999 | Williams et al. | |
| 6,031,854 A | 2/2000 | Lai | |
| 6,964,480 B2 * | 11/2005 | Levine | 351/211 |
| 2002/0013575 A1 | 1/2002 | Lai | |
| 2002/0030789 A1 * | 3/2002 | Campin | 351/209 |
| 2002/0154269 A1 * | 10/2002 | Liu et al. | 351/206 |
| 2004/0160576 A1 * | 8/2004 | Lai et al. | 351/211 |
| 2005/0024586 A1 * | 2/2005 | Teiwes et al. | 351/209 |

* cited by examiner

*Primary Examiner*—Jordan M. Schwartz

(57) ABSTRACT

The present invention contemplates to employ an eye-tracking device in an ophthalmic adaptive-optics system such that slow wavefront sensor and aberration-compensating element can be sufficient for the application. The present invention further contemplates to implement with the eye-tracking device a motion-compensating mechanism into the system such that the pupil images on both the wavefront sensor and the aberration-compensating element remain stationary during the operation of the system.

20 Claims, 2 Drawing Sheets

OPHTHALMIC ADAPTIVE-OPTICS DEVICE WITH A FAST EYE TRACKER AND A SLOW DEFORMABLE MIRROR

This application claims the benefit of U.S. Provisional Application No. 60/520,374, filed on Nov. 13, 2003.

FIELD OF THE INVENTION

The present invention relates to method and apparatus for constructing an adaptive optics instrument for ophthalmic applications. In particular, the present invention relates to method and apparatus for constructing an ophthalmic adaptive optics instrument with a fast eye tracker and a slow deformable mirror.

BACKGROUND OF THE INVENTION

Theory and experiments have demonstrated that adaptive optics can benefit many ophthalmic applications, such as improving the resolution of retina camera, improving the resolution of con-focal scanning laser tomography of the human fundus, and verifying surgical outcome prior a refractive laser surgery. To implement adaptive optics into these applications, a wavefront sensor and an aberration-compensating element are necessary to integrate into an ophthalmic instrument. The wavefront sensor is used to sense all optical aberrations of the eye and the aberration compensating element, e.g. a deformable mirror, is used to compensate these aberrations to make the eye a better optical imaging system.

For ophthalmic application of adaptive optics, the aberration of the eye is relatively stable while the eye itself may move rapidly. In a typical prior art ophthalmic adaptive optics system, both the wavefront sensor and the aberration-compensating element need to have a response time short enough to accommodate the eye movement. A characteristic eye movement can happen within a time interval of 5 ms to 100 ms. To make the wavefront sensor and the aberration-compensating element to response in such a time scale is found both challenging and expensive.

SUMMARY OF THE INVENTION

The present invention recognizes the difficulty with the prior art ophthalmic adaptive optics system and contemplates to employ an eye-tracking device to the system such that slow wavefront sensor and aberration-compensating element can be sufficient for the application. The present invention further contemplates to implement with the eye-tracking device a motion-compensating mechanism into the system such that the pupil images on both the wavefront sensor and the aberration-compensating element remain stationary during the operation of the system. One direct application of such an ophthalmic adaptive optics system is to provide patient-verified prescription of high order aberration for customized refractive surgery, as described in a pending application entitled method and apparatus for obtaining patient-verified prescription of high order aberration.

In one embodiment of the present invention, an ophthalmic adaptive-optics instrument is implemented with an observation target, a deformable mirror, a wavefront sensor, and an eye-tracking device. The eye-tracking device includes a sensing mechanism to sense the eye motion and a motion-compensating mechanism to compensate the eye motion. The instrument enables the patient to look at the observation target via the deformable mirror and the motion-compensating mechanism. The wavefront sensor senses the eye aberration also via the deformable mirror and the motion-compensating mechanism. The pupil image is relayed onto the deformable mirror and the wavefront sensor via the motion-compensating mechanism and thus remains constant at the deformable mirror regardless any eye movement. The wavefront sensor and the deformable mirror can, therefore, make aberration measurement and compensation within a time interval not limited by the eye movement.

Accordingly, an objective of the present invention is to provide a new and improved method and apparatus for an ophthalmic adaptive optics instrument.

Another objective of the present invention is to provide an ophthalmic adaptive-optics instrument with a fast eye tracker and a slow wavefront sensor and/or a slow aberration-compensating element.

A further objective of the present invention is to enable the use of slow deformable mirror for ophthalmic adaptive-optics applications.

The above and other objectives and advantages of the present invention will become more apparent in the following drawings, detailed description, and claims.

DETAILED DESCRIPTION OF THE DRAWINGS

Figure 1:
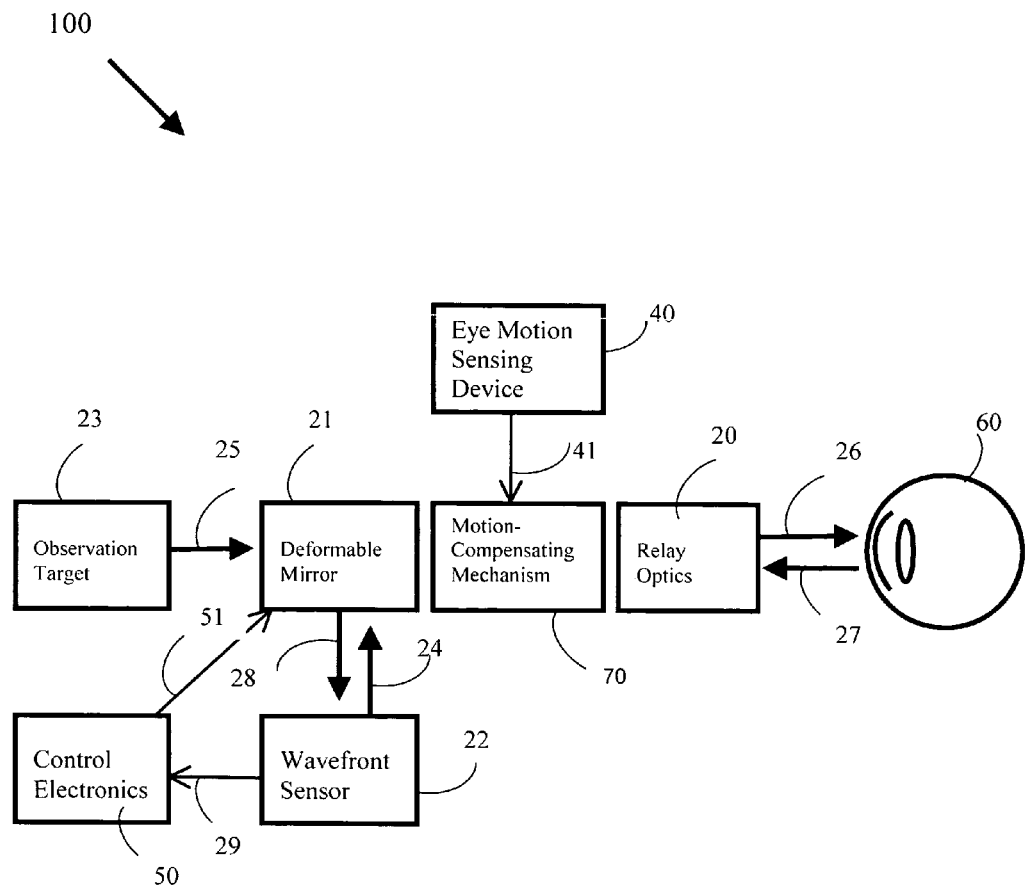
FIG. 1 shows schematically an ophthalmic adaptive-optics instrument employing an eye-motion compensating mechanism.

FIG. 1 shows schematically an ophthalmic adaptive-optics instrument 100 employing an eye-motion compensating mechanism 70, in accordance with the present invention. The ophthalmic adaptive-optics instrument 100 consists of relay optics 20, a deformable mirror 21, a wavefront sensor 22, an observation target 23, a control electronics 50, an eye motion sensing device 40, and a motion compensating mechanism 70.

The relay optics 20 relays the wavefront of an outgoing beam 27 from the pupil plane to the deformable mirror 21. The relay optics 20 comprises two or more lenses with all their own high order aberration well balanced and minimized. The relay optics 20 may include a set of compensation lenses or other mechanism to compensate low order aberration of the subject eye, such as defocusing and regular astigmatism. The construction and alignment of relay optics 20 are known to those skilled in the art.

The deformable mirror 21 is used here as an aberration-compensating element to modify or compensate wavefront distortion of a light beam impinging on it. The deformable mirror 21 is an adaptive-optics element and, driven by a programmable control signal 51, it can produce a position-dependent phase modulation across the beam. Therefore, the deformable mirror 21 works as a spatial phase modulator and can be replaced by other type of spatial phase modulators. The construction and control algorithm of a deformable mirror are known to those skilled in the art.

The wavefront sensor 22 projects a probe beam 24/26 into a subject eye 60 via the deformable mirror 21. The scattered light from the eye retina forms an outgoing beam 27 from the eye 60. This outgoing beam 27 passes through the deformable mirror 21 and turns into beam 28. The wavefront of the beam 28 is then measured with the wavefront sensor 22. The wavefront sensor 22 produces an output signal 29 indicating the aberration of the beam 28. The wavefront sensor 22 can be a Hartmann-Shack device. The construction and alignment of wavefront sensor 22 are known to those skilled in the art.

The observation target 23 is for the patient to fixate. It can have an illuminated starburst pattern or other patterns commonly used in ophthalmic instruments. The structure and alignment of observation target are known to those skilled in the art.

The control electronics 50 reads in the signal 29 and generates a control signal 51 to drive the deformable mirror 21. The deformable mirror 21 thus modifies and compensates the aberration of the subject eye 60 according to the control signal 51.

The eye motion-sensing device 40 is used to measure and monitor eye movement. The eye motion-sensing device 40 can be a camera based tracking device or a pupil-tracking device with x-y scanning beams. To be effective for the present application of ophthalmic adaptive-optics instrument, the sensing device 40 shall have a sensing rate 30 Hz or higher. The construction and alignment of the eye motion-sensing device 40 are known to those skilled in the art.

Figure 2:
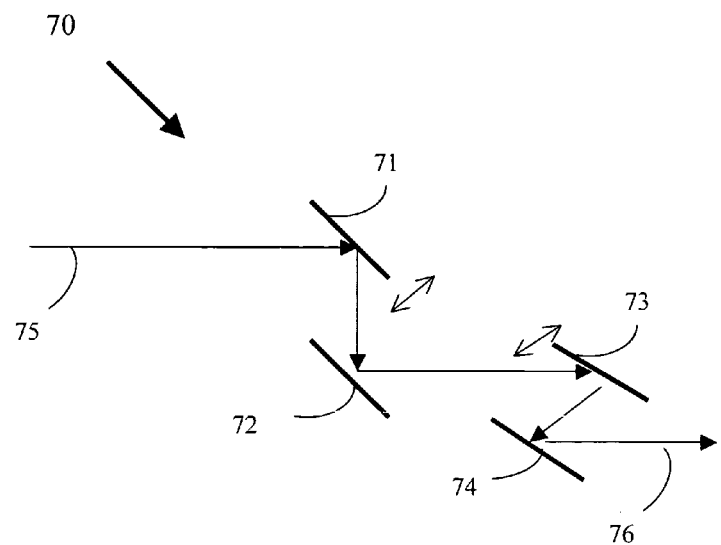
FIG. 2 shows schematically a motion-compensating mechanism to compensate eye movement.

The motion-compensating mechanism 70 is disposed in the optical path between the subject eye 60 and the deformable mirror 21. The motion-compensating mechanism 70 is driven by the eye motion-sensing device 40 to compensate the eye movement such that the pupil image on the deformable mirror 21 remains constant during the operation of the instrument. One design of a motion-compensating mechanism 70 is depicted in FIG. 2. Many designs of motion-compensating mechanism are known to those skilled in the art.

In operation, the patient's eye 60 looks at the observation target 23 through the deformable mirror 21 and the motion-compensating mechanism 70. The eye motion-sensing device 40 constantly senses the eye movement and drives the motion-compensating mechanism 70 to compensate the eye movement. The wavefront-sensing device 22 detects the wavefront aberration of the eye 60 via the deformable mirror 21 and the motion-compensating mechanism 70. The control electronics 50 is then to drive the deformable mirror 21 to make the measured wavefront aberration toward zero. As a result, the subject eye 60 can view the observation target 23 more sharply and clearly with the eye's aberration compensated.

As the eye movement is compensated by the movement-compensating mechanism 70, the pupil image on the deformable mirror 21, as well as on the wavefront-sensing device 22, is stationary. The wavefront measurement and the aberration compensation can thus be made within a time scale not limited to the eye movement. Practically, it is difficult to make accurate wavefront measurement and/or aberration compensation within 100 ms. With the implement of the eye motion-sensing device 40 and the motion-compensating mechanism 70, it becomes feasible to adapt a data acquisition time of wavefront sensing device 22 and a response time of deformable mirror 21 to be 100 ms or longer.

In the above embodiment of the present invention, the ophthalmic adaptive-optics instrument 100 is simply for a subject eye 60 to view an observation target 23 through an aberration compensating element, i.e. the deformable mirror 21. In application as a retina camera, the ophthalmic adaptive-optics instrument 100 shall include a retina camera viewing the subject retina through the deformable mirror 21. In application for con-focal scanning laser tomography, the ophthalmic adaptive-optics instrument 100 shall include a con-focal scanning laser ophthalscope viewing the subject fundus through the deformable mirror 21. The construction and alignment of retina camera or con-focal scanning laser ophthalscope are known to those skilled in the art.

FIG. 2 shows schematically a motion-compensating mechanism 70 to compensate for eye movement. The motion-compensating mechanism 70 consists of four turning mirrors 71, 72, 73 and 74. As shown in the figure, the mirrors 71 and 72 are arranged to make a vertical shift of the incoming beam 75, while mirrors 73 and 74 are arranged to make a horizontal shift of the incoming beam 75. The amount and sign of vertical shift can be changed through moving mirror 71 along its normal line. Similarly, the amount and sign of horizontal shift can be changed through moving mirror 73 along its normal line.

There shall be a driving mechanism to move each of mirror 71 and mirror 73. The driving mechanism, which is not shown in the figure, can be made with a translation stage driven by a step motor. The outgoing beam 76 can thus be shifted corresponding to the eye movement sensed by the eye motion-sensing device 40. To be effective for the application of the ophthalmic adaptive-optics instrument, the motion-compensating mechanism 70 shall have a response time of 30 ms or shorter.

Although the above description is based on preferred embodiments, various modifications can be made without departing from the scopes of the appended claims.

What is claimed is:

1. An ophthalmic adaptive-optics instrument comprising:
   an observation target disposed for a subject eye to fixate;
   an aberration-compensating element disposed in the observation path of said subject eye and receiving a pupil image through relay optics, wherein said aberration-compensating element is driven by a control signal and is capable to compensate low and high order aberration of said subject eye;
   a wavefront-sensing device sensing the aberration of said subject eye via said aberration-compensating element;
   control electronics coupled to said wavefront-sensing device to generate said control signal to drive said aberration-compensating element;
   an eye motion-sensing device sensing the movement of said subject eye; and
   a motion-compensating mechanism coupled to said eye motion-sensing device and disposed to compensate said movement of said subject eye, such that said pupil image stays stationary with respect to said aberration-compensating element;
   wherein said aberration-compensating element compensates said aberration of said subject eye while said motion-compensating mechanism compensates said movement of said subject eye.

2. An ophthalmic adaptive-optics instrument of claim 1, further comprising:
   a retina camera disposed to image the retina of said subject eye via said aberration-compensating element and said motion-compensating mechanism;
   wherein said ophthalmic adaptive-optics instrument is for retina imaging.

3. An ophthalmic adaptive-optics instrument of claim 1, further comprising:
   a con-focal scanning laser ophthalscope disposed to image the fundus of said subject eye via said aberration-compensating element and said motion-compensating mechanism;

wherein said ophthalmic adaptive-optics instrument is for con-focal scanning laser tomography.

4. An ophthalmic adaptive-optics instrument of claim 1, wherein said observation target is an illuminated starburst target.

5. An ophthalmic adaptive-optics instrument of claim 1, wherein said aberration-compensating element is a deformable mirror.

6. An ophthalmic adaptive-optics instrument of claim 1, wherein said aberration-compensating element consists of a deformable mirror and a set of compensation lenses.

7. An ophthalmic adaptive-optics instrument of claim 1, wherein said aberration-compensating element is a spatial phase modulator.

8. An ophthalmic adaptive-optics instrument of claim 1, wherein said aberration-compensating element has a response time longer than 100 ms.

9. An ophthalmic adaptive-optics instrument of claim 1, wherein said wavefront-sensing device is a Hartmann-Shack wavefront sensor.

10. An ophthalmic adaptive-optics instrument of claim 1, wherein said wavefront-sensing device has a data acquisition time longer than 100 ms.

11. An ophthalmic adaptive-optics instrument of claim 1, wherein said eye motion-sensing device is a camera based tracking device.

12. An ophthalmic adaptive-optics instrument of claim 1, wherein said eye motion-sensing device is a pupil tracking device employing x-y scanning beams.

13. An ophthalmic adaptive-optics instrument of claim 1, wherein said eye motion-sensing device has a sensing rate of 30 Hz or higher.

14. A method for constructing an ophthalmic adaptive-optics instrument, comprising the steps of:
   providing an observation target for a subject eye to fixate;
   providing an aberration-compensating element disposed in the observation path of said subject eye and receiving a pupil image through relay optics, wherein said aberration-compensating element is driven by a control signal and is capable to compensate low and high order aberration of said subject eye;
   providing a wavefront-sensing device to sense the aberration of said subject eye via said aberration-compensating element;
   providing control electronics coupled to said wavefront-sensing device;
   generating said control signal to drive said aberration-compensating element to compensate said aberration measured by said wavefront-sensing device;
   providing an eye motion-sensing device sensing the movement of said subject eye; and
   providing a motion-compensating mechanism coupled to said eye motion-sensing device and disposed to compensate said movement of said subject eye, such that said pupil image stays stationary with respect to said aberration-compensating element;
   wherein said aberration-compensating element compensates said aberration of said subject eye while said motion-compensating mechanism compensates said movement of said subject eye.

15. A method of claim 14, further comprising steps of:
   providing a retina camera disposed to image the retina of said subject eye via said aberration-compensating element and said motion-compensating mechanism;
   wherein said ophthalmic adaptive-optics instrument is for retina imaging.

16. A method of claim 14, further comprising steps of:
   providing a con-focal scanning laser ophthalscope disposed to image the fundus of said subject eye via said aberration-compensating element and said motion-compensating mechanism;
   wherein said ophthalmic adaptive-optics instrument is for con-focal scanning laser tomography.

17. An ophthalmic adaptive-optics instrument comprising:
   an observation target disposed for a subject eye to fixate;
   an aberration-compensating element disposed in the observation path of said subject eye and receiving a pupil image through relay optics, wherein said aberration-compensating element is driven by a control signal and is capable to compensate low and high order aberration of said subject eye;
   an eye motion-sensing device sensing the movement of said subject eye;
   a motion-compensating mechanism coupled to said eye motion-sensing device and disposed in said observation path of said subject eye, such that said pupil image remains stationary with respect to said aberration-compensating element;
   a wavefront-sensing device sensing the aberration of said subject eye via said motion-compensating mechanism and said aberration-compensating element; and
   control electronics coupled to said wavefront-sensing device to generate said control signal to drive said aberration-compensating element;
   wherein said aberration-compensating element compensates said aberration of said subject eye, while said motion-compensating mechanism compensates said movement of said subject eye.

18. An ophthalmic adaptive-optics instrument of claim 17, wherein said motion-compensating mechanism includes two pairs of folding mirrors.

19. An ophthalmic adaptive-optics instrument of claim 17, wherein said motion-compensating mechanism includes two folding mirrors moveable to compensate for horizontal and vertical displacements respectively.

20. An ophthalmic adaptive-optics instrument of claim 17, wherein said motion-compensating mechanism has a response time of 30 ms or shorter.

* * * * *